Figure 1:
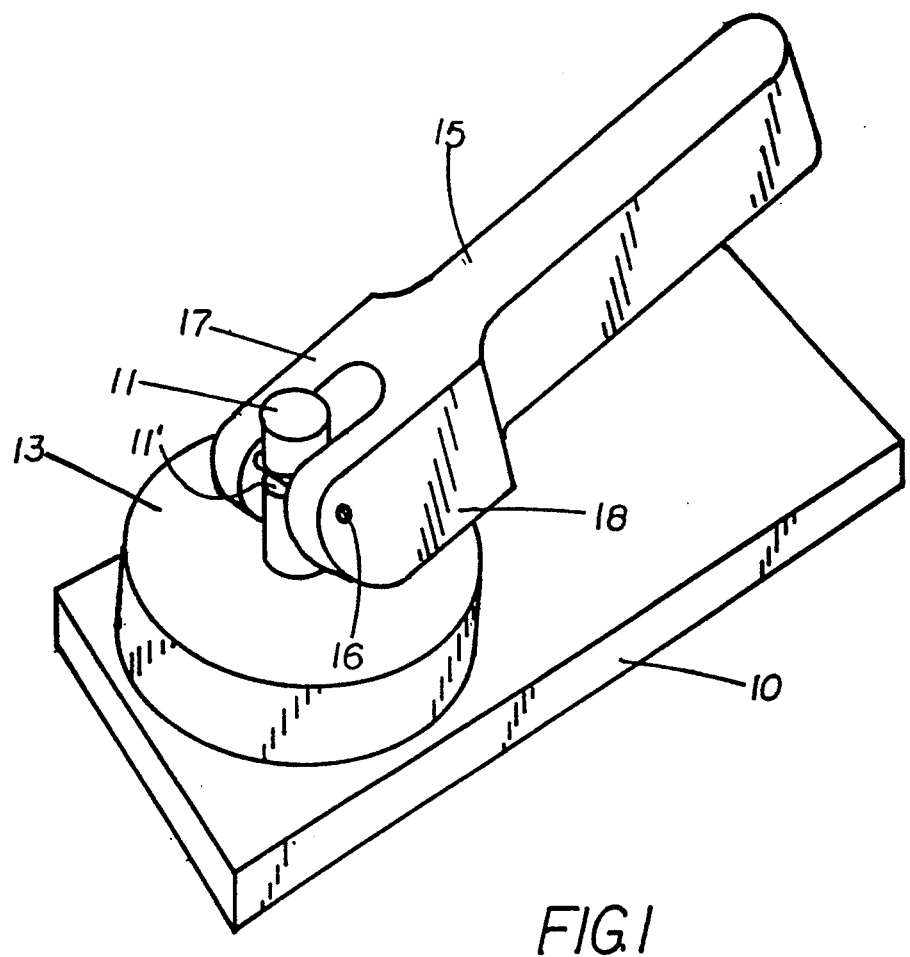

United States Patent [19]

Desmarais

[11] Patent Number: 5,361,664
[45] Date of Patent: Nov. 8, 1994

[54] STOMA WAFER CUTTING APPARATUS

[76] Inventor: Andrew R. Desmarais, 4 Maple St., Kennebunkport, Me. 04046

[21] Appl. No.: 27,108

[22] Filed: Mar. 5, 1993

[51] Int. Cl.⁵ ............................................ B26D 1/44
[52] U.S. Cl. ...................................... 83/628; 83/633; 83/698.91; 83/821
[58] Field of Search .......... 83/628, 633, 821, 698.91; 30/316

[56] References Cited

U.S. PATENT DOCUMENTS

| | | | |
|---|---|---|---|
| 2,739,379 | 3/1956 | Bassett | 30/28 |
| 4,391,042 | 7/1983 | Sunderland | 30/316 |
| 4,753,010 | 6/1988 | Franovich | 83/635 |
| 4,817,287 | 4/1989 | Arnold et al. | 30/316 |
| 4,858,317 | 8/1989 | Seib et al. | 30/316 |

Primary Examiner—Hien H. Phan

[57] ABSTRACT

A stoma wafer cutting apparatus with a base having an upwardly-extending projection over which a stoma wafer can be assembled, and a cutting unit including a circular cutting knife extending from its lower face for engagement with the stoma pad to effect the cutting of an enlarged hole therein and the upper end of the upstanding projection having a slot extending inwardly from its side face to the diameter of the projection. A hand-operating lever provided with a cross pin extending between depending spaced eccentric portions and adapted to enter the side slot of the projection on being assembled thereover for engagement of its rounded eccentric faces with the top surface of the cutting element. Upon application of pressure upon the lever, an enlarged hole will be cut in the stoma pad to render a hole suitable for receiving the user's particularly-sized stoma tube.

6 Claims, 2 Drawing Sheets

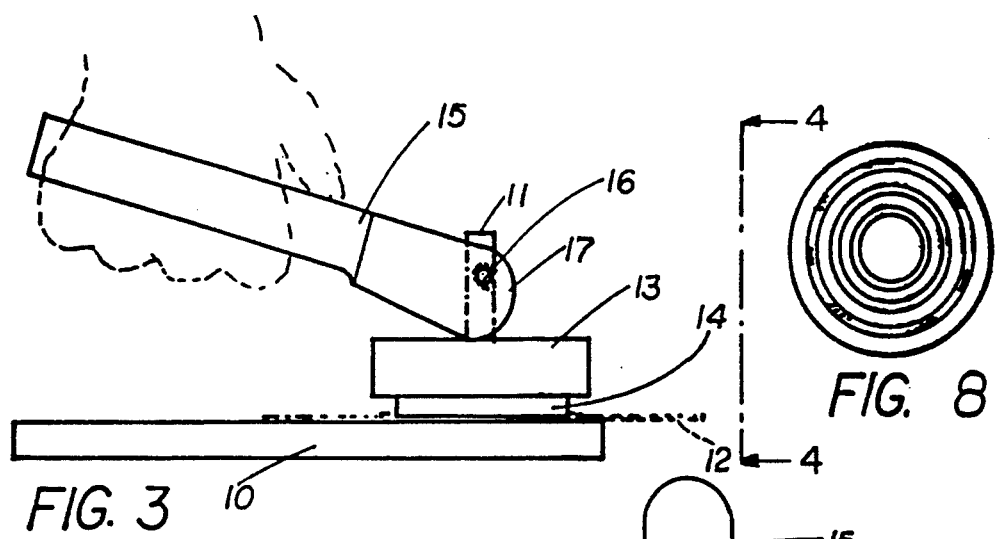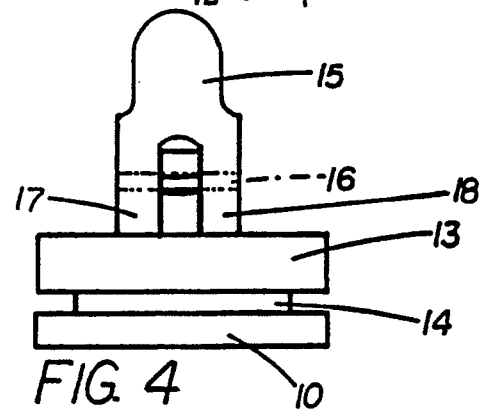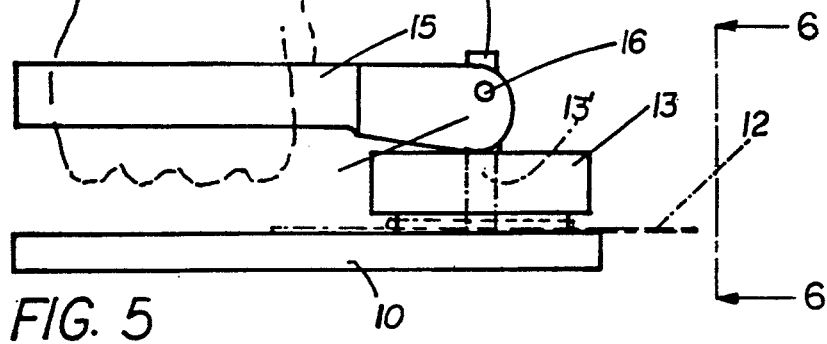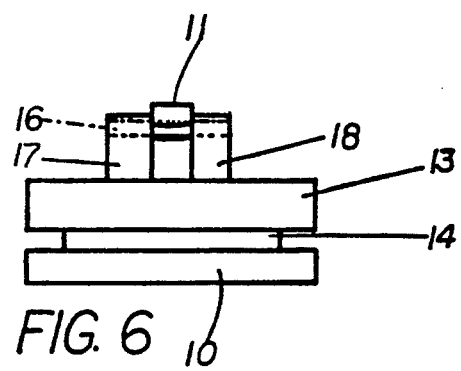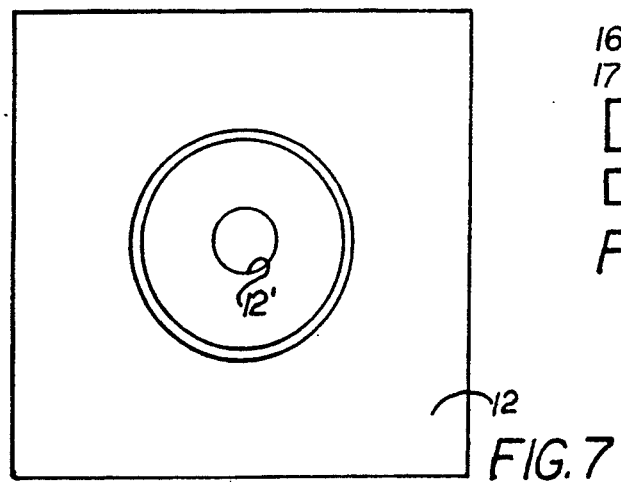

STOMA WAFER CUTTING APPARATUS

This invention relates to a cutting apparatus for enlarging openings in a stoma wafer used on the body of a person over the stoma opening for the purpose of supporting a waste receiving bag snapped in place thereupon.

Stoma wafers are formed of layers of plastic and rubber with a covering for the tacky surface which fastens the wafer to the body about the stoma opening. A plastic tube from the intestine extends through the stoma opening and through a stoma pad upon the stoma pad being attached thereto. Through the pad is a centrally disposed hole of usually less diameter than the plastic tube and often must be enlarged in order to accommodate a larger tube. The patient often finds it difficult to enlarge the opening upon these wafers when being placed upon the body surface. The only useable means available usually is a pair of scissors, and with them it is difficult to cut a clean opening without being jagged and to obtain the exact size for the tube that is to be extended therethrough. This problem is well set forth in U.S. Pat. No. 4,753,010 issued to Anthony Franovich issued on Jun. 28, 1988 when a stoma wafer cutting apparatus was developed for effecting the cutting of stoma wafers. There are also other showings of cutting wafers for this purpose in the patented art.

According to the present invention, there is provided a more simple construction of such a cutting apparatus that is operable in much the same manner as in the above-mentioned patent, but of fewer moveable disconnectable parts which can easily be disassembled and assembled for the insertion of the stoma wafer and for the application of the eccentric lever used to apply pressure to a cutting unit with a cutting disk. The cutting disk itself is grooved on the underside with various diameters and a circular cutting knife is selected to be placed in any one of the recesses according to the diametrical size of opening that is desired for the tube that is to be extended through the stoma wafer with the activating lever applied to the upper end of a projection extending upwardly from the base and adapted to receive a stoma wafer and the cutting unit placed thereover. Within the upper end of the projection is a cut slot extending laterally from the side face of the projection thereunto for receiving a cross pin extending between spaced side eccentric projections of the actuating lever. Upon the lever with a cross pin being assembled to the projection with the cross pin in the slot thereof and being turned down with the hand, the eccentric face formations on the lever will bear against the cutting unit to apply the cutting pressure upon the circular knife to effect a clean cut and the enlargement of the hole diameter. Thus, the user of these pads can readily have available a simple cutting apparatus for the cutting of the pads that have been acquired from the drugstore with but the small hole therein and permit the use of the larger diameter tubes to be extended from the stoma through stoma pads.

OBJECTS

It is, therefore, the principal object of the invention to provide a simple cutting apparatus with minimum parts adapted to be easily assembled by the user for cutting of his stoma pad with the desired diameter hole to accommodate his size tube.

It is another object of the invention to provide a stoma wafer cutting apparatus in which the operating handle with its eccentric projections can be easily assembled upon the upper end of the upstanding projection by mere uprighting of the handle to fit a cross pin into a side slot in a projection in which the handle is automatically locked as it is lowered with its eccentric projections engaging the top surface of the cutting unit to force the cutting action of its knife upon the stoma pad.

Other objects of the present invention are to provide a stoma pad or wafer cutting apparatus which has minimum parts, is of simple construction, consumes little space, is of pleasing appearance, is easy to use, is inexpensive and easy to operate.

DETAIL DESCRIPTION

Figure 2:
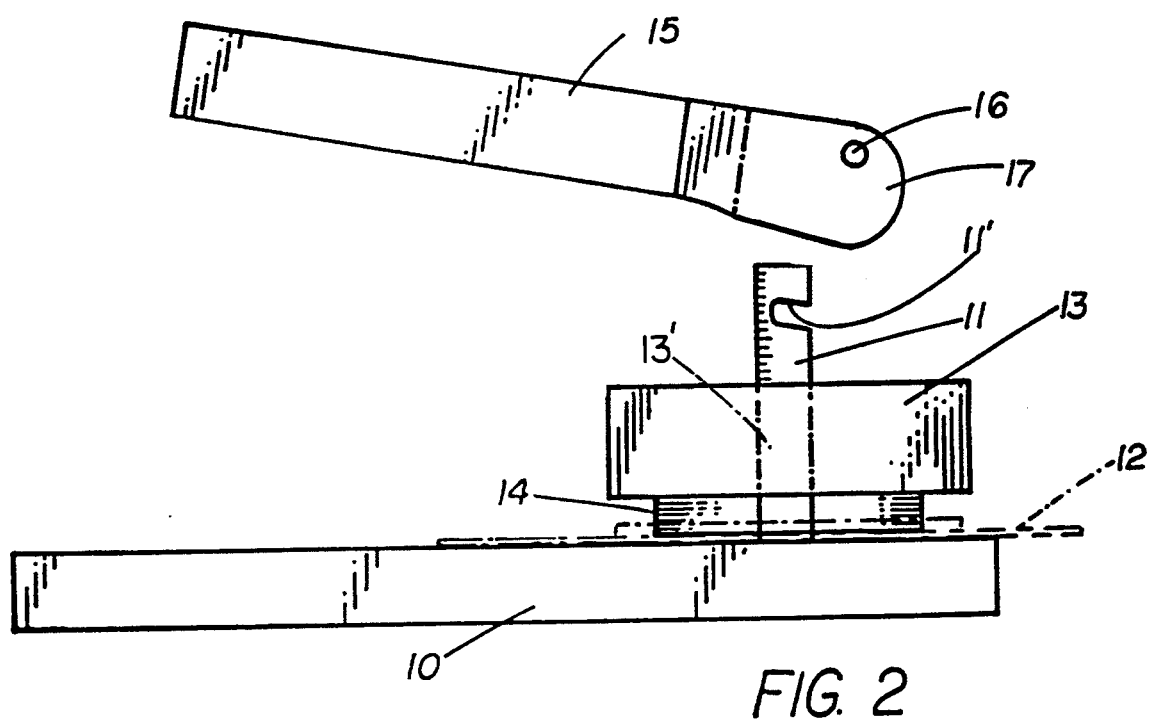

For a better understanding of this invention, reference can be had to the following detailed description taken in connection with the drawing, in which:

FIG. 1 is a top perspective view of the cutting apparatus of the present invention assembled without the stoma pad embodying the features of the present invention, FIG. 2 is a side elevational exploded view including the base with the upwardly-extending side-slotted projection with the cutting unit extended over a stoma pad shown in phantom and with the operating lever raised out of the slot and free of the projection, FIG. 3 is a side elevational view of the apparatus with the operating lever assembled thereon and with illustration made to lowering of the lever and forcing with its eccentric formations the downward thrust of the cutting unit to effect the cutting of an enlarged hole within a stoma pad, FIG. 4 is an end elevational view of the assembled apparatus upon its cutting unit being lowered as viewed on line 4—4 of FIG. 3 and looking in the direction of the arrows thereof, FIG. 5 is a side elevational view of the assembled apparatus with the operating unit fully lowered for the final cutting of the stoma pad, FIG. 6 is a forward end elevational view of the assembled apparatus with the eccentric formations fully lowered upon the cutting unit as viewed upon on line 6—6 and looking in the direction of the arrows thereof, FIG. 7 is a plan view of a stoma pad or wafer with its regular small centering hole therein, FIG. 8 is a bottom plan view of the cutting unit and the marking of the larger diameter to be cut indicated with a dotted line.

Referring now to FIG. 6 of the drawings, on line 6—6 of FIG. 5 and looking in the direction of the arrows thereof, 10 represents a base adapted to be supported on a tabletop, and upwardly from one end thereof there extends a side-slotted projection 11 over which a stoma wafer 12 (FIG. 5) is extended and supported on the top surface of the base 10 for the purpose of being cut. A stoma wafer 12 so assembled upon the base 10 is best seen in FIG. 2 and over which a cutting unit 13 with a circular cutting knife 14 is slid upon the side slotted projection 11 for its knife edge to engage with the stoma wafer 12. The cutting unit 13 has a central opening 13' to accommodate the side slot projection 11.

A hand-operating lever 15 is next assembled upon the sideslotted projection 11. This lever 15 has a cross pin 16 extending between spaced eccentric projections 17 and 18 that depend from the bottom side of the lever, and rounded at their forward ends to bear against the top of the cutting unit 13 as the lever is brought down from the position shown in FIGS. 3 and 4 to the final cut position shown in FIGS. 5 and 6. On assembly, the cross pin 16 is extended into a side slot 11', FIG. 2, of the projection 11. This side slot 11' is slightly inclined upwardly from the edge surface of the projection toward the diameter thereof. The eccentric portions effect the downward thrust of the cutting unit with their rounded end edges engaging with the top surface of the cutting unit.

It should be understood that the circular cutting knife 14 can be of any diameter in accordance with angular recesses disposed in the underface of the member 13. These recesses are not shown, but are well shown in the prior art. These different recesses permit the user of the device to select and use the diametrical size of cutter that is adapted for his particular size waste dispensing plastic tube. Upon purchase of the apparatus, the user would select the proper cutting knife for his purpose.

Upon the lever being depressed it will become tightly assembled to the upstanding projection 11, such that the apparatus without the stoma pad can be held together when not in use. It is to be understood that the lever 15 once it is turned upwardly from the projection can be easily slid out of the side slot 11' to permit the cutting unit to be removed to permit assembly or removal of the stoma pad 12 over or from the projection 11 and onto the base 10 as best seen in FIG. 2.

It should be apparent that there has now been provided a cutting apparatus for stoma pads that has minimum parts and is of simple construction such as to be suitable for many users.

While various changes may be made in the detail construction, it shall be understood that such changes shall be within the scope and spirit of the present invention as defined by the appended claims.

What is claimed is:

1. A stoma wafer cutting apparatus comprising:
   a base,
   a stoma wafer centering projection extending upwardly from the top surface of the base for receiving a stoma wafer having a centering aperture therein and requiring a larger diameter aperture to be cut therein, said projection having a side slot extending inwardly from its upper end for receiving a readily removable operating lever,
   an operating lever having spaced downwardly-extending eccentric portions and a cross pin extending between the spaced eccentric portions and adapted to be assembled/disassembled into the side slot of the projection without removing any other part of said apparatus,
   a cutting unit having a central opening therethrough slideable onto the upwardly-extending wafer centering projection with said side slot of said projection above an upper surface of said cutting unit,
   said eccentric portions of said operating lever having rounded, forward and eccentric faces adapted to engage with the upper surface of the cutting unit to effect cutting pressure for cutting of an enlarged aperture in the stoma wafer by lowering of the operating lever,
   and said lever being easily disassembled from said side slot in said centering projection upon raising of the operating lever to permit removal of said cutting unit and said wafer from said centering projection.

2. A stoma wafer cutting apparatus as defined in claim 1 and said side slot being inclined upwardly from its outer face toward its diameter while permitting the ready engagement/disengagement of the eccentric end faces of the spaced eccentric portions.

3. A stoma wafer cutting apparatus as defined in claim 1 wherein said stoma wafer has a circular centering therein and wherein said cutting apparatus further comprises:
   a cutting unit having a series of circular cutting blades for cutting different sized circular apertures in the wafer as desired by the user.

4. A stoma wafer cutting apparatus as defined in claim 1 wherein said base and said stoma wafer centering projection extending upwardly from the top surface of the base are integrally joined together in order to absorb the force of said lever on said cutting unit.

5. A stoma wafer cutting apparatus as defined in claim 1 wherein said operating lever further comprises at said force applying portion of said eccentric end thereof:
   an over center eccentric relief rearward of said force applying portion of said lever such that when the wafer has been cut and removed, the cutting unit can be replaced over said projection and said operating lever after engaging said pin can be moved to a downward position which holds the operational parts of said apparatus together for storage.

6. A stoma wafer cutting apparatus comprising:
   a base;
   a round stoma wafer centering projection extending upwardly from the top surface of the base for receiving a stoma wafer having a circular centering aperture therein and requiring a larger diameter aperture to be cut therein, said projection rigidly secured to said base at one end and having at the upper end thereof a side slot extending inwardly from its edge to about its diameter for receiving a readily removable operating lever;
   an operating lever having spaced downwardly-extending eccentric portions at one end thereof and a cross pin extending between the spaced eccentric portions; said lever being adapted to be assembled/disassembled into the side slot of the projection without removing any other part of said apparatus;
   a cutting unit having a central opening therethrough slideable onto the upwardly-extending wafer centering projection with said side slot of said projection located above an upper surface of said cutting unit;
   said eccentric portions of said operating lever having equally-shaped rounded, forward and lower eccentric faces adapted to engage with the upper surface of the cutting unit to effect sufficient cutting pressure for cutting an enlarged aperture in the stoma wafer by forcibly lowering the operating lever such that the eccentric faces move the cutting unit into the upper surface of said base;
   said lever being easily disassembled from said side slot in said centering projection upon raising of the operating lever to permit removal of said cutting unit and said wafer from said centering projection;
   said side slot being inclined upwardly from its outer face toward its diameter while permitting the ready engagement/disengagement of the eccentric end faces of the spaced eccentric portions for cutting and removal of said cut stoma wafer;

said stoma wafer having a circular centering aperture therein which fits over said projection;

a cutting unit having a series of circular cutting blades for cutting different sized circular apertures in the wafer as desired by the user;

said base and said stoma wafer centering projection extending upwardly from the top surface of the base are integrally joined together in order to absorb the force of said lever on said cutting unit; and an over center eccentric relief rearward of said force applying portion of said lever such that when the wafer has been cut and removed, the cutting unit can be replaced over said projection and said operating lever after engaging said pin can be moved to a downward position which holds the operational parts of said apparatus together for storage.

* * * * *